United States Patent [19]
Wardley et al.

[11] Patent Number: 5,718,901
[45] Date of Patent: Feb. 17, 1998

[54] FELINE CALICIVIRUS GENE

[75] Inventors: Richard Calvert Wardley, Hickory Corners; Leonard Edwin Post, Ann Arbor, both of Mich.

[73] Assignee: Pharmacia & Upjohn Company, Kalamazoo, Mich.

[21] Appl. No.: 463,579

[22] Filed: Jun. 5, 1995

Related U.S. Application Data

[62] Division of Ser. No. 221,539, Mar. 31, 1994, abandoned, which is a continuation of Ser. No. 60,481, May 11, 1993, abandoned, which is a continuation of Ser. No. 822,041, filed as PCT/US90/03753, Jul. 9, 1990, abandoned, which is a continuation of Ser. No. 408,989, Sep. 18, 1989, abandoned, which is a continuation of Ser. No. 383,908, Jul. 21, 1989, abandoned.

[51] Int. Cl.$^6$ .......... A61K 39/00; A61K 39/12; A61K 39/125; C07K 1/00
[52] U.S. Cl. ............ 424/184.1; 424/186.1; 424/187.1; 424/235.1; 424/216.1; 424/409; 530/350; 514/2
[58] Field of Search ............ 424/186.1, 184.1, 424/409, 235.1, 216.1, 187.1; 530/350; 514/2

[56] References Cited

U.S. PATENT DOCUMENTS

| | | | |
|---|---|---|---|
| 3,937,812 | 2/1976 | Bittle et al. | 424/89 |
| 4,031,204 | 6/1977 | Davis | 424/90 |

OTHER PUBLICATIONS

Lerner, R.A. et al. (1983) in: The Biology of Immunologic Disease, F.J. Dixon & D.W. Fisher, eds, HP Publishing Co, New York, NY, pp. 331–338.
Carter, M.J. et al (1989) J. Gen. Virol. 70:2197–2200.
Komolafe, O.O. et al. (1981) Virology. 110:217–220.
Neill, J.D. et al (1991) J. Virol 65: 5440–5447.
Tohya, Y. et al (1991) Arch. Virol. 117: 173–181.
Carter, M.J. et al. (1992) Arch. Virol. 122:223–225.
Ada, G.L. (1989) "Vaccines" in: *Fundamental Immunology*, Second Edition, W. E. Paul, ed., Raven Press, Ltd. NY, NY, pp. 985–1011.
Fretz et al. 1978 Virology 89: 318–321.
Black et al 1978 Nature 274: 614–615.
Black et al 1977 J. Gen. Virol. 38: 75–82.
D.W. Ehresmann and F.L. Schaffer, "RNA synthesized in calicivirus–infected cells is atypical of picornaviruses," J. Virol., 22, pp. 572–576 (1977).
D.W. Ehresmann and F.L. Schaffer, "Calicivirus Intracellular RNA: Fractionation of 18–22 S RNA and Lack of Typical 5'–Methylated Caps on 36 S and 22 S San Miguel Sea Lion Virus RNAs," Virology, 95, pp. 251–255 (1979).
D.N. Black, et al., "The structure and replication of calicivirus RNA," Nature, 274, pp. 614–615 (1978).
John D. Neill and William L. Mengeling, "Further Characterization of the Virus-Specific RNAs in Feline Calicivirus Infected Cells," Virus Research, 11, pp. 59–72 (1988).
M. Fretz and F.L. Schaffer, "Calicivirus proteins in infected cells: evidence for a capsid polypeptide precursor," Virology, 89, pp. 318–321 (1978).
D.N. Black and F. Brown, "Proteins induced by infection with caliciviruses," J. Gen. Virol., 38, pp. 75–82 (1977).

*Primary Examiner*—Nita Minnifield
*Attorney, Agent, or Firm*—James D. Darnley, Jr.

[57] ABSTRACT

The present invention provides recombinant DNA molecules comprising a sequence encoding a feline calicivirus polypeptide, particularly the capsid protein, host cells transformed by recombinant DNA molecule sequences, and the capsid polypeptides. The present invention also provides subunit vaccines and multivalent vaccines for FCV.

4 Claims, No Drawings

FELINE CALICIVIRUS GENE

CROSS-REFERENCE TO RELATED APPLICATIONS

This is a division of application Ser. No. 08/221,539, filed Mar. 31, 1994, now abandoned; which is a continuation of application Ser. No. 08/060,481, filed May 11, 1993, now abandoned; which is a continuation of application Ser. No. 07/822,041, filed Jan. 21, 1992, now abandoned; which is a 371 of PCT/US90/03753, filed Jul. 9, 1990, now pending; which is a continuation of application Ser. No. 07/408,989, filed Sep. 18, 1989, now abandoned; which is a continuation of application Ser. No. 07/383,908, filed Jul. 21, 1989, now abandoned.

FIELD OF INVENTION

This invention relates to recombinant DNA. More specifically, the invention relates to DNA sequences encoding feline calicivirus proteins and polypeptides related thereto. These DNA sequences are useful for screening animals to determine whether they are infected with feline calicivirus and also for expressing the polypeptides encoded thereby. The polypeptides may be used in diagnostic kits, as subunit vaccines and as multivalent vaccines comprising a different virus to protect cats against calicivirus infections.

BACKGROUND OF THE INVENTION

The caliciviruses are a family of small viruses which possess a plus-strand, non-segmented, polyadenylated RNA genome. The buoyant densities of these non-enveloped viruses range from 1.36 to 1.39 g/ml (Oglesby, A. S., et al., Biochemical and biophysical properties of vesicular exanthema of swine virus, Virology 44, pp. 329–341 (1971); Burroughs, J. N. and Brown, F., Physico-chemical evidence for re-classification of the caliciviruses, J. Gen. Virol., 22, pp. 281–285 (1974); Soergel, M. E., et al., Biophysical comparisons of calicivirus serotypes isolated from pinnipeds, Interviorology, 5, pp 239–244 (1975)). Members of this family include feline calicivirus (FCV), San Miguel sea lion virus (SMSV), vesicular exanthema virus of swine (VEV) and human calicivirus (Schaffer, F. L., Caliciviruses In: Comparative Virology, 14 (Fraenkel-Conrat, H. and Wagner, R., eds), pp. 249–284 (1979)).

There is increasing evidence that the caliciviruses are more widespread and may cause disease more often than was previously believed (Barlough, J. E., et al., Antibodies to marine caliciviruses in the pacific walrus, J. Wildlife Dis., 22, pp. 165–168 (1986); Cubbitt, W. D., et al., Winter vomiting disease caused by caliciviruses, J. Clin. Path., 32, pp. 786–793 (1979); Schaffer, F. L., et al., Characterization of a new calicivirus isolated from feces of a dog, Arch. Virol., 84, pp. 181–195 (1985); Smith, A. W., Marine reservoirs for caliciviruses, In: CRC Handbook Series in Zoonoses, Sect. B, Vol. II, pp. 182–190 (1981). Feline calicivirus is uniquitous in the cat population and has been demonstrated to cause disease (Gillespie, J. H. and Scott, F. W., Feline viral infections, Adv. Vet. Sci. Comp. Med., 17, pp. 163–200 (1973); Schaffer, F. L., Caliciviruses, In: Comparative Virology, 14, pp. 249–284 (1979). Very little is known concerning these viruses, and studies concerning the molecular biology and the relatedness of these viruses are lacking.

The signs of illness produced by FCV infections in the cat vary markedly, depending on the strain involved, the severity of the exposure and the resistance of the host. Some strains apparently cause little or no signs of illness. Strains of low virulence produce no or only moderate pyrexia but do produce ulcers of the tongue, hard palate and nose. Strains of high virulence produce pyrexia, anorexia, depression, dyspnea or polypnea and frequently death especially in neonatal animals. Ulcers of the tongue, hard palate and nose may, but do not always, occur in addition to pneumonic signs produced by the strains of high virulence. A FCV strain has also been implicated to some extent in causation of the urethritis-cystitis complex.

Although numerous serologically distinguishable FCV strains are recognized, they do have some common antigens. Cats with a demonstrable active immunity to one FCV strain often are resistant to disease if they are infected by other FCV strains. Therefore, a nonvirulent FCV strain may be broadly antigenic against many, but perhaps not all, strains of virulent as well as nonvirulent FCV.

FCV has been shown to be shed from the throat and in the feces of carrier cats for at least a year. Because recovered cats often become carriers, shedding accounts for the persistence of the virus in nature.

Morbidity from FCV infection tends to be high, and mortality in young kittens with severe signs of pneumonic disease may approach 100%. The mild form of the disease, characterized by lingual ulcers, is seldom fatal.

The major clinical features of the highly virulent or pneumonic FCV are fever, anorexia, depression and dyspnea or polypnea. The disease is first manifested as fever (104–105 F.) and anorexia. The fever tends to fluctuate after the initial elevation but the temperature tends to remain elevated through the course of the disease. Polypnea or dyspnea appears shortly after the initial fever rise, and moist rales may be ausculated. Depression tends to be marked and, except for the obvious respiratory distress, the infected cat may appear to be suffering from acute feline panleukopenia. Death occurs within days of the onset of signs. The pure pneumonic form of FCV infection appears to be most prevalent among neonatal (14–21 days old) and weaned kittens up to 4 months of age. Older susceptible cats exposed to the highly virulent FCVs may show initial signs suggestive of exudative pneumonia, which then becomes proliferative and interstitial as the cat recovers. In this age group, oral and nasal ulcers may occur noncurrently with the pneumonia.

Most vaccines used to control the feline respiratory disease complex contain a FCV component. Respiratory disease in cats is commonly caused by the different agents FCV, FHV and chlamydia spp. These agents can act together or singly and infection with one agent is clinically indistinguishable from infection with another. This complex etiology has led to vaccines containing antigens from each agent. The FCV is a nonpathogenic strain or one of very low virulence. However, resistance to challenge after parenteral injection of FCV vaccine is slow to develop. Even a successfully vaccinated cat may become infected and subsequently shed the challenge virus.

FCV's are excellent antigens and a vaccinated or previously infected cat develops high levels of systemic humoral antibodies. Kittens from such a queen receive maternal antibodies in the colostrum. Unfortunately, even kittens with high levels of passively transmitted antibodies may develop fatal pneumonic FCV infection when their respiratory tract is exposed to a highly virulent FCV. Apparently such a FCV can become well established in the lung before the circulating antibodies have a chance to diffuse to the affected area. In this type of situation, intranasal vaccination may be commenced in kittens as early as 1–2 weeks of age and repeated every 3 weeks in an attempt to provide local as well as systemic resistance. Unfortunately, this approach is not uniformly successful. Prophylaxis is then dependent on avoiding exposure to the virus by sanitation and isolation procedures. (Feline Medicine, P. W. Pratt, ed. pp. 97–99 (1983)).

As indicated above, there are many serotypes of FCV. Despite the number of serotypes, it is likely that there is sufficient cross neutralization among strains such that they should provide considerable cross-protection. It also appears that there are differences among strains in their pathogenicity. This has lead to the development of a vaccine that comprises a serotype of "low virulence" (F-9 virus), which protects against challenge with other serotypes. However, according to the Textbook of Veterinary Internal Medicine Diseases of the Dog and Cat, S. J. Ettinger, p. 292 (1983), "It is unfortunate that under some experimental [citation ommitted] and field conditions, the vaccine strain produces clinical signs of infection." The present invention seeks to overcome these problems by providing a subunit vaccine of FCV comprising a recombinantly produced calicivirus protein. Additionally provided is a "multi-valent vaccine" comprising the calicivirus gene cloned into another attenuated viral vector of another species (e.g., FHV) thereby providing protection against multiple species of virus. Such vaccines will not produce clinical signs of infection.

INFORMATION DISCLOSURE

In characterizations of viral-specific RNAs in calicivirus-infected cells, Ehresmann, D. W. and Schaffer, F. L., ("RNA synthesized in calicivirus-infected cells is atypical of picornaviruses," J. Virol., 22, pp. 572–576 (1977)) demonstrated that there are two calicivirus-specific transcripts in infected cells. Their work involved labeling experiments with FCV, SMSV and VEV-infected cells using $^3$H uridine in the presence of actinomycin D and subsequent analysis by glycerol gradient centrifugation and polyacrylamide gel electrophoresis. The largest RNA corresponded to the viral genomic RNA (36 S or approximately $2.6 \times 10^6$ daltons) and the other to a subgenomic RNA of approximately $1.1 \times 10^6$ daltons (22 S). They also demonstrated that approximately one-third of the viral RNA which sedimented at 18–22 S, was RNase resistant. This was shown to be the same size as the genomic RNA by analysis of the RNA on denaturing gradients and comparison to similarly treated 36 S RNA. Further work in characterization of the RNase-resistant population of RNAs which sedimented at 18–22 S showed that there were two double-stranded RNA species present, one of which corresponded to the genomic RNA and one to the 22 S subgenomic RNA (Ehresmann, D. W. and Schaffer, F. L., "Calicivirus intracellular RNA: fractionation of 18–22 S RNA and lack of typical 5'-methylated cap on 36 S and 22 S San Miguel Sea Lion Virus RNAs," Virology, 95, pp. 251–255 (1979)). Black, D. N., et al., ("The structure and replication of calicivirus RNA, Nature, 274, pp. 614–615 (1978)), in similar experiments with VEV, demonstrated the presence of the 36 S, 22 S and an 18 S RNA. In addition, the 18 S RNA was shown to be RNase-sensitive. They also noted the presence of a small amount of RNase-resistant RNA which also sedimented at 18 S. This, in concurrence with Ehresmann, D. W. and Schaffer, F. L., (supra), was considered to be double-stranded replicative form RNA.

J. D. Neill and W. L. Mengeling, "Further Characterization of the Virus-Specific RNAs in Feline Calicivirus Infected Cells", Virus Research, 11, pp. 59–72 (August 1988), which was published after the invention of the instant application, discloses the cDNA clones derived from the 3' end of the FCV genome of the instant application. This work resulted in the identification of a fourth single-stranded RNA, confirmation of the identity and size of the two double-stranded RNAs and the approximation of the length of each RNA transcript. Preliminary localization of each subgenomic RNA within the FCV genome was done through the hybridization of blotted RNA with cDNA clones originating from different regions of the genome and has demonstrated that the FCV RNAs are nested, co-terminal transcripts.

Fretz, M. and Schaffer, F. L., Calicivirus proteins in infected cells: evidence for a capsid polypeptide precursor, Virology, 89, pp. 318–321 (1978) proposed that the capsid protein may be the translational product of the 22 S RNA. The 2.4 kb RNA is present in high copy number and the capsid protein is the most abundant viral protein present in calicivirus infected cells (Black, D. N. and Brown, F., Proteins induced by infection with caliciviruses, J. Gen. Virol., 38, pp. 75–82 (1977); Fretz, M. and Schaffer, F. L., Calicivirus proteins in infected cells: evidence for a capsid polypeptide precursor, Virology, 89, pp. 318–321 (1978).

SUMMARY OF THE INVENTION

The present invention provides recombinant DNA molecules comprising DNA sequences encoding polypeptides displaying FCV immunogenicity.

More particularly, the present invention provides host cells transformed with recombinant DNA molecules comprising the DNA sequence set forth in Chart A and fragments thereof.

The present invention also provides polypeptides expressed by hosts transformed with recombinant DNA molecules comprising DNA sequence of the formula set forth in Chart A and immunologically functional equivalents and immunogenic fragments and derivatives of the polypeptides.

More particularly, the present invention provides polypeptides having the formula set forth in Chart B, immunogenic fragments thereof and immunologically functional equivalents thereof.

The present invention also provides recombinant DNA molecules comprising the DNA sequences encoding FCV capsid protein or immunogenic fragments thereof, in particular, a feline herpesvirus having the FCV coat protein gene inserted therein.

The present invention also provides a method for detecting FCV infections in animals comprising contacting a DNA sequence of the present invention with fluid from an animal to be diagnosed, and also diagnostic assays using the FCV polypeptides of the invention.

DETAILED DESCRIPTION OF THE INVENTION

As used herein, immunogenicity and antigenicity are used interchangeably to refer to the ability to stimulate any type of adaptive immune response, i.e., antigen and antigenicity are not limited in meaning to substances that stimulate the production of antibodies.

Most of the recombinant DNA methods employed in practicing the present invention are standard procedures, well known to those skilled in the art, and described in detail, for example, in Molecular Cloning, T. Maniatis, et al., Cold Spring Harbor Laboratory, (1982) and B. Perbal, A Practical Guide to Molecular Cloning, John Wiley & Sons (1984), which are incorporated herein by reference.

All restriction endonucleases, *E. coli* DNA polymerase I, *E. coli* DNA polymerase Klenow fragment, T4 DNA ligase, T4 DNA polymerase, EcoRI methylase and *E. coli* DNA ligase were purchased from New England Biolabs (Beverly, Mass.). AMV reverse transcriptase was purchased from Bio-Rad (Richmond, Calif.). RNase H was from Bethesda Research Laboratories (Gaithersburg, Md.), and RNasin RNase inhibitor was from Promega Biotech (Madison, Wis.). Lambda gt10 and gigapack in vitro packaging system were purchased from Stratagene Cloning Systems (San Diego, Calif.). [$\alpha$-$^{35}$S]dATP was from New England Nuclear (Boston, Mass.) and [$\alpha$-$^{32}$S]dATP was purchased from ICN Radiochemical (Irvine, Calif.).

FCV strain CFI/68 FIV was obtained from the American Type Culture Collection. FCV was propagated in Crandall-Reese Feline Kidney cells (CRFK) which were maintained in F-15 Eagle's MEM supplemented with 0.25% lactalbumin hydrolysate and 10% fetal calf serum. FCV was plaque-purified to eliminate defective interfering particles.

*E. coli* strain DH1 (D. Hanahan, J. Mol. Biol., 166, pp. 557–80 (1983)) was used for plasmid maintenance and propagation and was maintained on Luria broth (LB) agar plates which contained 50 µg/ml ampicillin when plating transformed bacteria. Strain C600 (Appleyard, R. K., Genetics, 39, pp. 440–452 (1954)) was used for plating lambda gt10 and was maintained and plated on NZY-amine agar plates. Strain JM107 (Yanisch-Perron et al., Gene, 33, pp. 103–119 (1985)) was used for transformation by pUC plasmids (Yanisch-Perron et al., supra) and was plated on LB plates containing 80 µg IPTG and 0.01% X-gal per plate. JM107 was also used to propagate M13mp18 containing FCV cDNA clones for dideoxy chain termination sequence analysis. JM107 was maintained on minimal medium as previously described (Yanisch-Perron et al., supra).

FCV was propagated by infection of CRFK cells, which had been grown to confluence in 490 cm$^2$ roller bottles, with FCV at an m.o.i. of approximately 0.01 in a total volume of 10 ml. The virus was allowed to adsorb for 2 hours at 37° C. The inoculum was removed and 50 ml of serum-free medium was added and the incubation was continued at 37° C. until CPE was complete (generally within 24 hours). The medium was removed and was frozen at –20° C., thawed at room temperature and the cell debris was removed by centrifugation at 5000 rpm for 10 min at 4° C. in a Sovall GS-3 rotor. The virus was precipitated from the supenatant by the addition of solid polyethylene glycol (PEG, 8000 M$_r$) to final concentration of 10% (w/v) and stirring at room temperature until the PEG was in solution. The precipitate was pelleted by centrifugation at 8000 rpm for 20 minutes in the GS-3 rotor and the supernatant was discarded. The pellet was resuspended in 10 ml of phosphate buffered saline (PBS, pH 7.2), the insoluble matter was removed by centrifugation at 10.000 rpm for 10 minutes in a Sovall 8A-600 rotor and the supernatant was layered over a CsCl step gradient. The step gradient was formed by layering 5 ml of 1.28 g/ml CsCl over 5 ml of 1.60 g/ml CsCl, both in PBS, and immediately layering the VCV supernatant on the top of the gradient. The virions (p=1.36) were banded at the 1.60:1.28 interface by centrifugation at 22,000 rpm for 3 hours at 4° C. in a SW28 rotor. The white viral band was removed and was rebanded in an isopyknic CsCl gradient (1.38 g/ml CsCl) by centrifugation at 48,000 rpm for 18 hours in a 70.1 TI rotor. The viral band was removed from the gradient and was dialyzed against 1000 volumes of PBS overnight. The purified virions were stored at –70° C.

For Northern blot analysis, total cellular poly(A)$^+$ RNA from FCV-infected cells (approximately 3 µg) was separated on formaldehyde denaturing agarose gels according to the procedure of Lehrach, H., et al., Biochemistry, 16, pp. 4743–4751 (1977). The RNA was blotted to nitrocellulose, prehybridized and hybridized with $^{32}$P-labeled FCV cDNA clones according to the procedure of Thomas, P. S., Hybridization of denatured RNA and small DNA fragments transferred to nitrocellulose, Proc. Natl. Acad. Sci. USA, 77, pp. 5201–5205 (1980). Autoradiography was done without intensifying screens using Kodak XAR-5 film.

EXAMPLE 1

Preparation of FCV RNA and Cloning and Screening of FCV cDNA

Full-length genomic FCV RNA was prepared from isolated virions as previously described (Love, D. N., Cornell Vet., 66, pp. 498–512 (1976)). Total cellular RNA was prepared from FCV-infected and non-infected cells by the guanidine-HCl:CsCl centrifugation procedure as described by Krawetz, S. A. and Anwar, R. A., Biotechniques, 2, pp. 342–347 (1984). CRFK cells were grown and inoculated as described above with the exception that the cells were inoculated at an m.o.i. of approximately 10. Total poly(A)$^+$ RNA was isolated by oligo(dT) cellulose chromatography according to Maniatis, T., et al., supra. FCV double-stranded RNA was LiCl fractionated from total cellular RNA isolated from FCV infected cells as described by Garger, S. J. and Turpen, T. H., Methods Enzymol., 118, pp. 717–722 (1986).

First-strand cDNA was synthesized from FCV genomic RNA using oligo(dT) as primer and with AMV reverse transcriptase as specified by the supplier. Second-strand cDNA was synthesized according to Gubler, U. and Hoffman, B. J., Gene, 25, pp. 263–269 (1983). The ends of the double-stranded cDNA were made blunt with T4 DNA polymerase, the cDNA was treated with EcoRI methylase and EcoRI synthetic linkers were blunt-end ligated onto the cDNA. The cDNA-linker mixture was digested with EcoRI and was precipitated twice with an equal volume of 4M ammonium acetate and 2 volumes of ethanol. The cDNA was then ligated into lambda gt10, in vitro packaged and plated on appropriate *E. coli* strains. The resultant plaques were lifted on nitrocellulose filters and probed with $^{32}$P-labeled random-primed cDNA which had been synthesized using the FCV genomic RNA as template as described by Maniatis, T., et al., supra. A second library was also constructed in the same manner using PstI linkers and ligation into PstI-digested pUC18. This was done because only the large internal EcoRI fragment was recovered from the lambda library.

A synthetic oligonucleotide 20 mer GGAATTTTGCCCCGGGCCCT, synthesized on an Applied Biosystems Oligonucleotide Synthesizer (model 8750), was used to prime first strand cDNA synthesis in order to clone FCV sequences 5' to those contained within pCV2 (Chart C). This sequence was derived from DNA sequence analysis of the end of the EcoRI fragment which corresponded to the 5' end of the cloned FCV genome. cDNA was synthesized and cloned as described above with PstI synthetic linkers. The cDNA was cloned into pUC18, used to transform JM107 and screened by plating on medium containing IPTG and X-gal as previously described.

The ends of FCV cDNA clones were sequenced using the dideoxy chain termination procedure as described by Williams, S. A., et al., Biotechniques, 4, pp. 138–147 (1986) to allow synthesis of the synthetic oligonucleotide primer described above for further cloning of the FCV genome and to determine which strand encoded the viral sense strand by location of the cloned poly(A) tail.

The cDNA library of FCV sequences constructed in the lambda cloning vector gt10 was screened with $^{32}$P-labeled random-primed cDNA which was synthesized using FCV genomic RNA as the template. A plaque with a strong hybridization signal was isolated and found to contain an EcoRI fragment of approximately 4200 bp. This fragment was subcloned into pUC18 for restriction enzyme analysis (Chart C). The resulting plasmid was designated pCV2.

The second cDNA library was constructed using PstI linkers in the plasmid pUC18. White transformants were analyzed for the presence of cDNA inserts by gel electrophoresis and a plasmid containing an insert of approximately 1000 bases was chosen for analysis. This plasmid, pCV7, was subjected to restriction analysis and was found to contain restriction sites in common with pCV2 and also contained a region of approximately 500 bp which contained novel restriction sites (Chart C). The PstI fragment was subcloned into M13mp18 and the ends, in both orientations, were sequenced. One of these sequences showed a poly(A) tract of 46 adenine residues, demonstrating that this clone contained the 3' end of the FCV genome. From this analysis, it was possible to determine which strand encoded the viral sense strand and to place the clones in the proper orientation.

Once it was known which strand encoded the FCV sense strand, the sequence at the EcoRI site which corresponded to the 5' portion of the cloned FCV RNA contained in PCV2 was determined. From this information, a synthetic oligonucleotide was synthesized which hybridized to sequences approximately 150 bases 3' of the 5'-most EcoRI sequence of the genomic RNA. This oligonucleotide was used to prime reverse transcription in order to clone sequences 5' of the EcoRI restriction site. The double-stranded cDNA was blunt-ended, cloned with PstI linkers, and analyzed as described above. A plasmid containing an insert of approximately 2800 bases was chosen for further analysis. Restriction endonuclease analysis showed that this clone contained restriction sites in common with the 5' end of pCV2 as well as a region of approximately 2000 bases of novel sequences. This plasmid was designated pCV8. The results of the restriction endonuclease mapping are illustrated in Chart C.

EXAMPLE 2

Location of cDNAs in Calicivirus Genome

Northern blots of FCV-infected total cellular poly(A)$^+$ RNA were probed with FCV cDNA clones corresponding to different regions of the FCV genome. This was done to approximate the location from which the different subgenomic RNAs are derived. The location within the genome of these cDNA clones is illustrated in Chart A. Probing with pCV3 produced the characteristic 4 bands corresponding to the four FCV RNAs, while probing with pCV6 resulted in the loss of signal from the 2.4 kb transcript. This result demonstrates that the 2.4 kb transcript is derived from within the 3' 3000 bases of the FCV genome. Probing with pCV9 demonstrated that the genomic RNA is present as is the 4.8 kb transcript. This indicates that there is only a small region of homology between this transcript and the FCV sequences contained in pCV9. Probing with pCV10 yielded only the full-length genomic RNA indicating that the 4.2 and 4.8 kb transcripts are encoded 3' of the position of this cDNA probe and that the 4.8 kb transcript originates within the sequences contained in pCV9. A diagram illustrating the results of this mapping is shown in Chart D.

These results demonstrate that the cDNA clone from the 3' end of the FCV genome hybridizes with all of the FCV transcripts. As the probes used are progressively more 5' within the genome, there is a progressive loss of hybridization signal from the 2.4 kb to the 4.8 kb transcripts. This demonstrates that the RNAs are co-terminal, nested sets of transcripts in which the transcript begins at specific points and then continues to the 3' end of the genome.

EXAMPLE 3

Diagnosis of FCV Infections Using Proteins Encoded by Cloned cDNA Probes

In this example we describe the use of cloned FCV cDNA encoded polypeptides as diagnostics to identify FCV infections in cats. The cDNA clones are operably linked to functional control elements (e.g., promoter) and used to express FCV proteins in appropriate vectors, e.g., *E. coli* and baculovirus. The proteins so expressed are used in a number of different immunoassays. Such procedures could include a solid phase enzyme linked immunosorbent assay in which feline FCV antibodies from a cat to be tested would bind to the protein used as the basis for the ELISA. Competitive ELISA's could also be used where a monoclonal antibody directed against the FCV protein acts as part of the detection system. Other solid phase support systems, e.g., beads, paper strips, etc., could also act as the anchor for the protein and be developed as a "pet side" test for FCV antibody detection.

EXAMPLE 4

Insertion of the FCV Coat Protein Gene into Baculovirus

The FCV capsid protein gene can be engineered for expression in a variety of systems by standard methods. Knowledge of the sequence of the capsid protein gene plus availability of vectors are required for a skilled molecular biologist to construct expression vectors that would be useful to make the capsid for use as a vaccine. This is an example of production of the capsid as a subunit.

The C-terminal half of the coding region is constructed as follows. The EcoRV/EcoRI fragment, spanning from position 1350 to 1965 (Chart A) is isolated (e.g., from pCV2, Chart C) and cloned between the EcoRV and PstI sites of a modified pUC19 vector with an EcoRV linker inserted at the SmaI site with the following synthetic oligonucleotides inserted to reconstruct the C-terminal coding region of the capsid protein and provide a linker to the PstI site: 5'-AATTCAATTGGCAAAAATTCGACTTGCCTCTAACA-TFAGGAGTGTGATGACAAAATTATGAATTAGATCT-ACTGCA-3' and 5'-GTAGATCTAATTCATAATTTTGTC-ATCACACTCCTAATGTTAGAGGCAAGTCGAATTTTT-GCCAATTG-3'. This plasmid is designated pFCV-C.

The N-terminal half of the capsid gene is engineered by cloning the BamHI/EcoRV fragment from position 62 through 1350 between the EcoRV and BamHI sites of pBR322. This plasmid is opened with BamHI plus SalI and the following synthetic oligonuecleotides inserted to re-construct the rest of the N-terminal coding region of the capsid protein: 5'-TCGACAGATCTCCGCGGTTTGAGCATGTGCTCAA-CCTGCGCTAACGTGCTTAAATACTATGATTG-3' and 5'-GATCCAATCATAGTATTTAAGCACGTTAGCGCAG-GTTGAGCACATGCTCAAACCGCGGAGATCTG-3'. This plasmid is designated pFCV-N.

The FCV sequences from pFCV-C are isolated with EcoRV and PstI, and the FCV sequences from pFCV-N are isolated with SalI plus EcoRV. These fragments are combined and cloned between the EcoRI and SalI sites of pUC19 to give a plasmid designated pCOAT, which contains an intact FCV coat protein gene.

Because of the additional synthetic DNA placed on the end of the coat protein gene in pCOAT, the intact FCV coat protein gene can be excised from this plasmid as a BglII fragment, which can be inserted downstream from the baculovirus polyhedrin promoter in the standard baculovirus expression plasmid pAc373. By co-transfection with baculovirus (e.g., Autographa californica nuclear polyhedrosis virus) DNA and picking occlusion negative plaques, viruses expressing the coat protein gene can be isolated. The baculovirus techniques are set forth in PCT/US88/02021, publication WO 89/00196, 12 Jan. 1989, and incorporated herein by reference. This coat protein can be used crude or purified for injection into cats as a vaccine for feline calicivirus.

Convenient restriction enzyme sites are synthesized on the 3' and 5' ends of the coat protein gene.

For expression in baculovirus, the gene is inserted downstream from the Ac NPV polyhedrin promoter and recombined into a baculovirus genome according to the procedure set forth in PCT/US88/02021, publication WO 89/00196, 12 Jan. 1989, and incorporated here by reference. Such a protein is useful as a subunit vaccine.

EXAMPLE 5

Insertion of the FCV Coat Protein Gene into Feline Herpesvirus

We have previously described use of a SalI/BamHI piece of the feline herpesvirus 1 (FHV) genome containing the thymidine kinase gene. In previous work, the thymidine kinase encoding nucleotides between the EcoRI and HindIII cleavage sites have been deleted, and a unique HindIII site inserted in the place of these nucleotides, to provide a plasmid, pGC113 with a unique insertion site into the thymidine kinase gene. (See PCT/US89/03289, publication WO 90/01547, 22 Feb. 1990, and incorporated herein by reference) An oligonucleotide containing a PstI cleavage site was inserted into the deleted thymidine kinase gene of pGC113 to give pFHVTK-P. This plasmid is used as a recipient for the FCV gene engineered for expression in mammalian cells.

The pFCV-C plasmid is cleaved with BglII plus PstI, and the bovine growth hormone polyadenylation signal PvuII/EcoRI fragment is inserted with a BamHI linker on the PvuII end and a PstI linker on the EcoRI end (linkers added in separate steps with cloning intermediates, by standard methods). The PvuII/EcoRI fragment is shown in European Patent 91 73552. This BamHI linker ligates to the BglII site but does not regenerate either a BamHI or BglII site. The resulting plasmid is designated pFCV-C-PA. An EcoRV/PstI fragment containing the FCV sequences and polyadenylation signal is excised, mixed with the SalI/EcoRV fragment from pFCV-N, and cloned between the PstI and SalI sites of pUC19 to yield a plasmid designated pCOAT-PA.

pCOAT-PA is cleaved with Pst plus SacII and the coat protein gene plus polyadenylation signal isolated as a SacII/PstI fragment.

A PstI/SacII fragment containing the major immediate early promoter of cytomegalovirus Towne strain can be isolated from pON239 (Spaete and Mocarski, J. Virol., 56, 135–143, 1985), which is available from Dr. Ed Mocarski, Stanford University.

pFHVTK-P cut with PstI is then mixed the two fragments isolated in the preceding two paragraphs, ligated, and a plasmid isolated which contains: the CMV promoter—FCV coat protein—bGH polyadenylation signal transcription unit inserted into the FHV thymidine kinase gene. This plasmid is designated pCOAT-TK.

pCOAT-TK is transfected with DNA from a wild type strain of FHV into Crandall-Reese feline kidney cells and thymidine kinase negative recombinants selected with thymidine arabinoside, as described in detail in PCT/US89/03289, publication WO 90/01547, 22 Feb. 1990 (supra). These recombinants will express FHV, and can be used for vaccination of cats by intramuscular or intranasal inoculation.

The availability of the gene sequences of the present invention permits direct manipulation of the genes and gene sequences which allows modifications of the regulation of expression and/or the structure of the protein encoded by the gene or a fragment thereof. Knowledge of these gene sequences also allows one to clone the corresponding gene, or fragment thereof, from any strain of FCV using the known sequence as a hybridization probe, and to express the entire protein or fragment thereof by recombinant techniques generally known in the art.

Knowledge of these gene sequences (the capsid protein is encoded by bases 18–2021, see Chart A) enabled us to deduce the amino acid sequence of the capsid (or coat). corresponding polypeptides (Chart B). As a result, fragments of these polypeptides having FCV immunogenicity can be produced by other standard methods of protein synthesis or recombinant DNA techniques.

By "derivatives" of such DNA sequences is meant to include base substitutions done to the degeneracy of the code and also known base analogs inserted therein. The primary structure (sequence) of the gene coding, inter alia, for the capsid (or coat) protein from FCV also is set forth in Chart A.

The excised gene or fragments thereof can be ligated to various cloning vehicles or vectors for use in transforming a host cell. The vectors preferably contain DNA sequences to initiate, control and terminate transcription and translation (which together comprise expression) of the FCV polypeptide genes and are, therefore, operatively linked thereto. These "expression control sequences" are preferably compatible with the host cell to be transformed. When the host cell is a higher animal cell, e.g., a mammalian cell, heterologous expression control sequences are employed. The vectors additionally preferably contain a marker gene (e.g., antibiotic resistance) to provide a phenotypic trait for selection of transformed host cells. Additionally a replicating vector will contain a replicon.

Typical vectors are plasmids, phages, and viruses that infect animal cells. In essence, one can use any DNA sequence that is capable of transforming a host cell.

The term host cell as used herein means a cell capable of being transformed with the DNA sequence coding for a polypeptide displaying FCV polypeptide antigenicity. Preferably, the host cell is capable of expressing the FCV polypeptide or fragments thereof. The host cell can be procaryotic or eucaryotic. Illustrative procaryotic cells are bacteria such as E. coli, B. subtilis, Pseudomonas, and B. stearothermophilus. Illustrative eucaryotic cells are yeast or higher animal cells such as cells of insect, plant or mammalian origin. Mammalian cell systems often will be in the form of monolayers of cells although mammalian cell suspensions may also be used. Mammalian cell lines include, for example, VERO and HeLa cells, Chinese hamster ovary (CHO) cell lines, W138, BHK, COS-7 or MDCK cell lines.

Insect cell lines include the Sf9 line of *Spodoptera frugiperda* (ATCC CRL1711). A summary of some available eucaryotic plasmids, host cells and methods for employing them for cloning and expressing FCV polypeptides can be found in K. Esser, et al., Plasmids of Eukaryotes (Fundamentals and Applications), Springer-Verlag (1986) which is incorporated herein by reference.

As indicated above, the vector, e.g., a plasmid, which is used to transform the host cell preferably contains compatible expression control sequences for expression of the FCV polypeptide gene or fragments thereof. The expression control sequences are, therefore, operatively linked to the gene or fragment. When the host cells are bacteria, illustrative useful expression control sequences include the trp promoter and operator (Goeddel, et al., Nucl. Acids Res., 8, 4057 (1980)); the lac promoter and operator (Chang, et al., Nature, 275, 615 (1978)); the outer membrane protein promoter (EMBO J., 1, 771–775 (1982)); the bacteriophage λ promoters and operators (Nucl. Acids Res., 11, 4677–4688 (1983)); the α-amylase (*B. subtilis*) promoter and operator, termination sequences and other expression enhancement and control sequences compatible with the selected host cell. When the host cell is yeast, illustrative useful expression control sequences include, e.g., α-mating factor. For insect cells the polyhedrin promoter of baculoviruses can be used (Mol. Cell. Biol., 3, pp. 2156–65 (1983)). When the host cell is of insect or mammalian origin illustrative useful expression control sequences include, e.g., the SV-40 promoter (Science, 222, 524–527 (1983)) or, e.g., the metallothionein promoter (Nature, 296, 3942 (1982)) or a heat shock promoter (Voellmy, et al., Proc. Natl. Acad. Sci. USA, 82, pp. 4949–53 (1985)).

The plasmid or replicating or integrating DNA material containing the expression control sequences is cleaved using restriction enzymes, adjusted in size as necessary or desirable, and ligated with the FCV polypeptide gene or fragments thereof by means well known in the art. When yeast or higher animal host cells are employed, polyadenylation or terminator sequences from known yeast or mammalian genes may be incorporated into the vector. For example, the bovine growth hormone polyadenylation sequence may be used as set forth in European publication number 0 093 619 which is incorporated herein by reference. Additionally gene sequences to control replication of the host cell may be incorporated into the vector.

The host cells are competent or rendered competent for transformation by various means. When bacterial cells are the host cells they can be rendered competent by treatment with salts, typically a calcium salt, as generally described by Cohen, PNAS, 69, 2110 (1972). A yeast host cell generally is rendered competent by removal of its cell wall or by other means such as ionic treatment (J. Bacteriol., 153, 163–168 (1983)). There are several well-known methods of introducing DNA into animal cells including, e.g., calcium phosphate precipitation, fusion of the recipient cells with bacterial protoplasts containing the DNA, treatment of the recipient cells with liposomes containing the DNA, and microinjection of the DNA directly into the cells. Electroportion may also be used to insert DNA into cells.

The transformed cells are grown up by means well known in the art (Molecular Cloning, Maniatis, T., et al., Cold Spring Harbor Laboratory, (1982); Biochemical Methods In Cell Culture And Virology, Kuchler, R. J., Dowden, Hutchinson and Ross, Inc., (1977); Methods In Yeast Genetics, Sherman, F., et al., Cold Spring Harbor Laboratory, (1982)) and the expressed FCV polypeptide or fragment thereof is harvested from the cell medium in those system where the protein is excreted from the host cell, or from the cell suspension after disruption of the host cell system by, e.g., mechanical or enzymatic means which are well known in the art.

There are several convenient methods that can be used to express the FCV genes of the present invention. For example, the capsid protein gene can be inserted in the feline herpesvirus genome as set forth in the example relating to feline leukemia virus gp85 in PCT/US89/03289, publication WO 90/01547, 22 Feb. 1990, which is incorporated herein by reference. The FCV gene of interest is cloned downstream from the human CNV immediate early promoter and flanked with the FHV thymidine kinase sequence. This plasmid is co-transfected with the FHV DNA thymidine kinase deficient recombinants are selected by thymidine arabinoside. The recombinant FHV so produced, comprising the FCV gene of interest, expresses the FCV polypeptide encoded thereby.

The FCV genes of interest can also be inserted in the vaccinia virus according to the method of Mackett, et al, in DNA Cloning, Volume II, A Practical Approach, D. M. Glover, ed. (1985), with the improvement comprising using pSC11 as the plasmid vector as described by Chakrabarty et al, Mol. Cell Biol., 5, 3403–09 (1985). The method is essentially described in PCT application PCT/US86/01761, publication WO 87/02058 which is incorporated herein by reference, except that the pSC11 vector is substituted for pGS20.

As noted above, the amino acid sequences of the FCV polypeptides as deduced from the gene structures are set forth in Charts A and B. Polypeptides displaying FCV polypeptide antigenicity include the sequences set forth in Charts A and B and any portions of the polypeptide sequences which are capable of eliciting an immune response in an animal, e.g., a mammal, which has been injected with the polypeptide sequence and also immunogenically functional analogs of the polypeptides.

As indicated hereinabove the entire gene coding for the FCV polypeptide can be employed in constructing the vectors and transforming the host cells to express the FCV polypeptide, or fragments of the gene coding for the FCV polypeptide can be employed, whereby the resulting host cell will express polypeptides displaying FCV antigenicity. Any fragment of the FCV polypeptide gene can be employed which results in the expression of a polypeptide which is an immunogenic fragment of the FCV polypeptide or an analog thereof. As is well known in the art, the degeneracy of the genetic code permits easy substitution of base pairs to produce functionally equivalent genes, fragments and derivatives thereof encoding polypeptides displaying FCV polypeptide antigenicity. These functional equivalents also are included within the scope of the invention.

Additionally, it is considered that there may be only certain fragments of the entire amino acid sequence of the FCV polypeptides, together with their spacing and interrelationship with other fragments which are primarily for the FCV immunogenicity. Thus, except for those critical fragments which are primarily responsible for the FCV immunogenicity, a further interchange of amino acids or other materials in the FCV gene sequences is acceptable.

A vaccine prepared utilizing a polypeptide of the instant invention or an immunogenic fragment thereof can consist of fixed host cells, a host cell extract, or a partially or completely purified FCV polypeptide preparation from the host cells or produced by chemical synthesis. The FCV polypeptide immunogen prepared in accordance with the present invention is preferably free of FCV virus. Thus, the vaccine immunogen of the invention is composed substantially entirely of the desired immunogenic FCV polypeptide and/or other FCV polypeptides displaying FCV antigenicity.

The immunogen can be prepared in vaccine dose form by well-known procedures. The vaccine can be administered intramuscularly, subcutaneously or intranasally. For parenteral administration, such as intramuscular injection, the immunogen may be combined with a suitable carrier, for example, it may be administered in water, saline or buffered vehicles with or without various adjuvants or immunomodulating agents including aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionobacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.). Another suitable adjuvant is Freund's Incomplete Adjuvant (Difco Laboratories, Detroit, Mich.).

The proportion of immunogen and adjuvant can be varied over a broad range so long as both are present in effective amounts. For example, aluminum hydroxide can be present in an amount of about 0.5% of the vaccine mixture ($Al_2O_3$ basis). On a per dose basis, the concentration of the immunogen can range from about 1.0 μg to about 100 mg per cat. A preferable range is from about 100 μg to about 3.0 mg per cat. A suitable dose size is about 1–10 ml, preferably about 1.0 ml. Accordingly, a dose for intramuscular injection, for example, would comprise 1 ml containing 1.0 mg of immunogen in admixture with 0.5% aluminum hydroxide. Comparable dose forms can also be prepared for parenteral administration to kittens, but the amount of immunogen per dose may be smaller, for example, about 0.25 to about 1.0 mg per dose.

The vaccine may also be combined with other vaccines for other diseases to produce multivalent vaccines. It may also be combined with other medicaments, for example, antibiotics. A pharmaceutically effective amount of the vaccine can be employed with a pharmaceutically acceptable carrier or diluent to vaccinate animals such as swine, cattle, sheep, goats, and other mammals.

Other vaccines may be prepared according to methods well known to those skilled in the art as set forth, for example, in I. Tizard, An Introduction to Veterinary Immunology, 2nd ed. (1982), which is incorporated herein by reference.

CHART A.
cDNA from Calicivirus

```
         10         20         30         40         50         60
    GTGTTCGAAG TTTGAGCATG TGCTCAACCT GCGCTAACGT GCTTAAATAC TATGATTGGG
    CACAAGCTTC AAACTCGTAC ACGAGTTGGA CGCGATTGCA CGAATTTATG ATACTAACCC 70         80         90        100        110        120
    ATCCTCACAT CAAATTGGTA ATCAACCCCA ACAAATTTCT ACATGTTGGC TTCTGCGATA
    TAGGAGTGTA GTTTAACCAT TAGTTGGGGT TGTTTAAAGA TGTACAACCG AAGACGCTAT 130        140        150        160        170        180
    ACCCTTTAAT GTGTTGTTAT CCTGAATTAC TACCTGAATT TGGCACCATG TGGGATTGTG
    TGGGAAATTA CACAACAATA GGACTTAATG ATGGACTTAA ACCGTGGTAC ACCCTAACAC 190        200        210        220        230        240
    ATCAATCGCC ACTCCAAGTC TACCTTGAGT CAATCCTGGG TGATGATGAA TGGTCCTCCA
    TAGTTAGCGG TGAGGTTCAG ATGGAACTCA GTTAGGACCC ACTACTACTT ACCAGGAGGT 250        260        270        280        290        300
    CTCATGAAGC AATTGACCCA GTTGTGCCAC CAATGCATTG GGATGAAGCC GGAAAAATCT
    GAGTACTTCG TTAACTGGGT CAACACGGTG GTTACGTAAC CCTACTTCGG CCTTTTTAGA 310        320        330        340        350        360
    TCCAACCACA CCCTGGCGTC CTTATGCATC ACCTCATCTG TAAGGTTGCA GAAGGATGGG
    AGGTTGGTGT GGGACCGCAG GAATACGTAG TGGACTAGAC ATTCCAACGT CTTCCTACCC 370        380        390        400        410        420
    ACCCAAACCT GCCACTTTTC CGCTTGGAAG CGGACGATGG TTCCATCACG ACACCTGAAC
    TGGGTTTGGA CGGTGAAAAG GCGAACCTTC GCCTGCTACC AAGGTAGTGC TGTGGACTTG 430        440        450        460        470        480
    AGGGAACAAT GGTTGGTGGA GTCATTGCTG AGCCCAACGC CCAAATGTCA ACCGCAGCTG
    TCCCTTGTTA CCAACCACCT CAGTAACGAC TCGGGTTGCG GGTTTACAGT TGGCGTCGAC 490        500        510        520        530        540
    ACATGGCCAC TGGGAAAAGT GTGGACTCTG AGTGGGAAGC CTTCTTCTCC TTTCACACTA
    TGTACCGGTG ACCCTTTTCA CACCTGAGAC TCACCCTTCG GAAGAAGAGG AAAGTGTGAT 550        560        570        580        590        600
    GTGTGAACTG GAGCACATCT GAAACTCAGG GGAAGATACT CTTTAAACAA TCCTTAGGAC
    CACACTTGAC CTCGTGTAGA CTTTGAGTCC CCTTCTATGA GAAATTTGTT AGGAATCCTG 610        620        630        640        650        660
    CATTGCTCAA CCCCTACCTT ACCCATCTTG CAAAGCTGTA TGTTGCTTGG TCTGGTTCTG
    GTAACGAGTT GGGGATGGAA TGGGTAGAAC GTTTCGACAT ACAACGAACC AGACCAAGAC
```

-continued
CHART A.
cDNA from Calicivirus

| | | | | | |
|---|---|---|---|---|---|
| 670 | 680 | 690 | 700 | 710 | 720 |
| TTGATGTTAG | GTTTTCTATT | TCTGGATCTG | GTGTCTTTGG | AGGGAAATTA | GCTGCTATTG |
| AACTACAATC | CAAAAGATAA | AGACCTAGAC | CACAGAAACC | TCCCTTTAAT | CGACGATAAC |
| 730 | 740 | 750 | 760 | 770 | 780 |
| TTGTGCCGCC | AGGAATTGAT | CCTGTTCAAA | GTACTTCAAT | GCTGCAATAT | CCTCATGTCC |
| AACACGGCGG | TCCTTAACTA | GGACAAGTTT | CATGAAGTTA | CGACGTTATA | GGAGTACAGG |
| 790 | 800 | 810 | 820 | 830 | 840 |
| TCTTTGATGC | TCGTCAAGTT | GAACCTGTTA | TCTTTTCCAT | TCCCGATCTA | AGAAGCACCT |
| AGAAACTACG | AGCAGTTCAA | CTTGGACAAT | AGAAAAGGTA | AGGGCTAGAT | TCTTCGTGGA |
| 850 | 860 | 870 | 880 | 890 | 900 |
| TATATCACCT | TATGTCTGAC | ACTGATACCA | CATCGTTGGT | AATCATGGTG | TACAATGATC |
| ATATAGTGGA | ATACAGACTG | TGACTATGGT | GTAGCAACCA | TTAGTACCAC | ATGTTACTAG |
| 910 | 920 | 930 | 940 | 950 | 960 |
| TTATTAACCC | CTATGCTAAT | GACTCAAACT | CTTCGGGCTG | CATTGTCACT | GTGGAAACTA |
| AATAATTGGG | GATACGATTA | CTGAGTTTGA | GAAGCCCGAC | GTAACAGTGA | CACCTTTGAT |
| 970 | 980 | 990 | 1000 | 1010 | 1020 |
| AACCGGGGCC | AGATTTCAAG | TTTCACCTCT | TAAAACCTCC | TGGGTCTATG | TTAACTCACG |
| TTGGCCCCGG | TCTAAAGTTC | AAAGTGGAGA | ATTTTGGAGG | ACCCAGATAC | AATTGAGTGC |
| 1030 | 1040 | 1050 | 1060 | 1070 | 1080 |
| GATCTATCCC | ATCTGATCTA | ATCCCAAAAT | CATCTTCGCT | TTGGATTGGA | AATCGGTTTT |
| CTAGATAGGG | TAGACTAGAT | TAGGGTTTTA | GTAGAAGCGA | AACCTAACCT | TTAGCCAAAA |
| 1090 | 1100 | 1110 | 1120 | 1130 | 1140 |
| GGTCTGACAT | AACCGATTTT | GTAATTCGGC | CTTTTGTGTT | CCAGGCAAAT | CGACACTTTG |
| CCAGACTGTA | TTGGCTAAAA | CATTAAGCCG | GAAAACACAA | GGTCCGTTTA | GCTGTGAAAC |
| 1150 | 1160 | 1170 | 1180 | 1190 | 1200 |
| ATTTCAACCA | AGAGACAGCA | GGTTGGAGCA | CCCCAAGGTT | TCGCCCAATT | ACTATCACTA |
| TAAAGTTGGT | TCTCTGTCGT | CCAACCTCGT | GGGGTTCCAA | AGCGGGTTAA | TGATAGTGAT |
| 1210 | 1220 | 1230 | 1240 | 1250 | 1260 |
| TCAGTGTTAA | GGAGTCAGCA | AAGCTTGGTA | TTGGAGTGGC | CACCGACTAC | ATTGTTCCCG |
| AGTCACAATT | CCTCAGTCGT | TTCGAACCAT | AACCTCACCG | GTGGCTGATG | TAACAAGGGC |
| 1270 | 1280 | 1290 | 1300 | 1310 | 1320 |
| GCATACCAGA | TGGATGGCCC | GACACAACAA | TCCCAGGTGA | GTTGGTACCT | GTTGGTGACT |
| CGTATGGTCT | ACCTACCGGG | CTGTGTTGTT | AGGGTCCACT | CAACCATGGA | CAACCACTGA |
| 1330 | 1340 | 1350 | 1360 | 1370 | 1380 |
| ATGCCATCAC | TAATGGCACC | AACAATGATA | TCACCACAGC | TGCGCAGTAC | GATGCAGCCA |
| TACGGTAGTG | ATTACCGTGG | TTGTTACTAT | AGTGGTGTCG | ACGCGTCATG | CTACGTCGGT |
| 1390 | 1400 | 1410 | 1420 | 1430 | 1440 |
| CTGAGATTAG | AAACAACACC | AATTTCAGAG | GCATGTACAT | TTGTGGTTCT | CTTCAAAGAG |
| GACTCTAATC | TTTGTTGTGG | TTAAAGTCTC | CGTACATGTA | AACACCAAGA | GAAGTTTCTC |
| 1450 | 1460 | 1470 | 1480 | 1490 | 1500 |
| CTTGGGGGGA | TAAGAAGATT | TCAAATACTG | CTTTTATCAC | AACCGGCACG | GTTGATGGAG |
| GAACCCCCCT | ATTCTTCTAA | AGTTTATGAC | GAAAATAGTG | TTGGCCGTGC | CAACTACCTC |
| 1510 | 1520 | 1530 | 1540 | 1550 | 1560 |
| CCAAATTGAT | ACCCAGTAAT | ACCATTGACC | AAACAAAAAT | TGCCGTATTC | CAAGACACAC |
| GGTTTAACTA | TGGGTCATTA | TGGTAACTGG | TTTGTTTTTA | ACGGCATAAG | GTTCTGTGTG |
| 1570 | 1580 | 1590 | 1600 | 1610 | 1620 |
| ATGCGAATAA | GCATGTCCAG | ACCTCGGACG | ACACATTGGC | CCTGCTTGGT | TATACTGGTA |
| TACGCTTATT | CGTACAGGTC | TGGAGCCTGC | TGTGTAACCG | GGACGAACCA | ATATGACCAT |
| 1630 | 1640 | 1650 | 1660 | 1670 | 1680 |
| TTGGTGAGGA | AGCAATTGGT | GCTGACCGCG | ATAGAGTTGT | GCGAATTAGC | GTCCTCCCGG |
| AACCACTCCT | TCGTTAACCA | CGACTGGCGC | TATCTCAACA | CGCTTAATCG | CAGGAGGGCC |
| 1690 | 1700 | 1710 | 1720 | 1730 | 1740 |
| AACGTGGCGC | ACGTGGTGGC | AATCACCCAA | TCTTCCACAA | AAACTCTATC | AAGCTTGGTT |
| TTGCACCGCG | TGCACCACCG | TTAGTGGGTT | AGAAGGTGTT | TTTGAGATAG | TTCGAACCAA |
| 1750 | 1760 | 1770 | 1780 | 1790 | 1800 |
| ATGTAATTAG | GTCCATTGAT | GTGTTCAATT | CTCAAATTCT | GCATACCTCT | AGGCAACTTT |
| TACATTAATC | CAGGTAACTA | CACAAGTTAA | GAGTTTAAGA | CGTATGGAGA | TCCGTTGAAA |
| 1810 | 1820 | 1830 | 1840 | 1850 | 1860 |
| CCCTCAATCA | TTACTTATTG | TCGCCTGACT | CCTTTGCTGT | CTATAGGATT | ATTGACTCTA |
| GGGAGTTAGT | AATGAATAAC | AGCGGACTGA | GGAAACGACA | GATATCCTAA | TAACTGAGAT |

CHART A.
cDNA from Calicivirus

```
         1870       1880       1890       1900       1910       1920
    ATGGATCCTG GTTTGACATA GGCATTGATA ATGATGGATT TTCTTTTGTT GGTGTATCAA
    TACCTAGGAC CAAACTGTAT CCGTAACTAT TACTACCTAA AAGAAAACAA CCACATAGTT 1930       1940       1950       1960       1970       1980
    GTATTGGTAA ATTAGAGTTT CCTTTAACTG CCTCCTACAT GGGAATTCAA TTGGCAAAAA
    CATAACCATT TAATCTCAAA GGAAATTGAC GGAGGATGTA CCCTTAAGTT AACCGTTTTT 1990       2000       2010       2020       2030       2040
    TTCGACTTGC CTCTAACATT AGGAGTGTGA TGACAAAATT ATGAATTCAA TTTTGGGCTT
    AAGCTGAACG GAGATTGTAA TCCTCACACT ACTGTTTTAA TACTTAAGTT AAAACCCGAA 2050       2060       2070       2080       2090       2100
    AATTGACACT GTCACGAACA CAATTGGCAA AGCTCAACAA ATCGAATTGG ATAAGGCTGC
    TTAACTGTGA CAGTGCTTGT GTTAACCGTT TCGAGTTGTT TAGCTTAACC TATTCCGACG 2110       2120       2130       2140       2150       2160
    ACTTGGTCAG CAACGCGACC TGGCACTCCA ACGTATGAAC TTGGATCGCC AGGCTCTAAA
    TGAACCAGTC GTTGCGCTCG ACCGTGAGGT TGCATACTTG AACCTAGCGG TCCGAGATTT 2170       2180       2190       2200       2210       2220
    TAATCAAGTG GAGCAATTTA ACAAACTGCT TGAGCAGAGG GTACAAGGCC CAATCCAATC
    ATTAGTTCAC CTCGTTAAAT TGTTTGACGA ACTCGTCTCC CATGTTCCGG GTTAGGTTAG 2230       2240       2250       2260       2270       2280
    TGTGCGCCTG GCACGCGCAG CTGGTTTCAG GGTCGACCCT TACTCATACA CAAATCAAAA
    ACACGCGGAC CGTGCGCGTC GACCAAAGTC CCAGCTGGGA ATGAGTATGT GTTTAGTTTT 2290       2300       2310       2320       2330       2340
    CTTTTATGAC GATCAATTAA ATGCAATCAG ACTATCATAT AGAAATTTGT TCAAGAATTG
    GAAAATACTG CTAGTTAATT TACGTTAGTC TGATAGTATA TCTTTAAACA AGTTCTTAAC 2350       2360       2370       2380
    ATCACTTAAC CCTTTGGGTG CCGCACTTGC GCCTAACCCC AGGGA
    TAGTGAATTG GGAAACCCAC GGCGTGAACG CGGATTGGGG TCCCT
```

Chart B. Calicivirus Coat Protein

| | | | | | |
|---|---|---|---|---|---|
| 1 | MCSTCANVLK | YYDWDPHIKL | VINPNKFLHV | GFCDNPLMCC | YPELLPEPGT |
| 51 | MWDCDQSPLQ | VYLESILGDD | EWSSTHEAID | PVVPPMHWDE | AGKIFQPHPG |
| 101 | VLMHHLICKV | AEGWDPNLPL | FRLEADDGSI | TTPEQGTMVG | GVIAEPNAQM |
| 151 | STAADMATGK | SVDSEWEAFF | SFHTSVNWST | SETQGKILFK | QSLGPLLNPY |
| 201 | LTHLAKLYVA | WSGSVDVRFS | ISGSGVFGGK | LSAIVVPPGI | DPVQSTSMLQ |
| 251 | YPHVLFDARQ | VEPVIFSIPD | LRSTLYHLMS | DTDTTSLVIM | VYNPLINPYA |
| 301 | NDSNSSGCIV | TVETKPGPDF | KFHLLKPPGS | MLTHGSIPSD | LIPKSSSLWI |
| 351 | GNRFWSDITD | FVIRPFVFQA | NRHFDFNQET | AGWSTPRFRP | ITITISVKES |
| 401 | AKLGIGVATD | YIVPGIPDGW | PDTTIPGELV | PVGDYAITNG | TNNDITTAAQ |
| 451 | YDAATEIRNN | TNFRGMYICG | SLQRAWGDKK | ISNTAFITTG | TVDGAKLIPS |
| 501 | NTIDQTKIAV | FQDTHANKHV | QTSDDTLALL | GYTGIGEEAI | GADRDRVVRI |
| 551 | SVLPERGARG | GNHPIFHKNS | IKLGYVIRSI | DVFNSQILHT | SRQLSLNHYL |
| 601 | LSPDSFAVYR | IIDSNGSWFD | IGIDNDGFSF | VGVSSIGKLE | PPLTASYMGI |
| 651 | QLAKIRLASN | IRSVMTKL | | | |

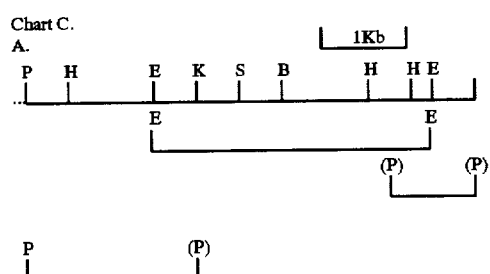

(A) Physical map of feline calicivirus (FCV) cDNA. Restriction endonuclease cleavage sites are indicated. Dots at 5' end of genome represent uncloned sequences. Lines beneath the map indicate cDNA clones that were obtained following cloning of reverse transcribed genomic RNA as described in Example 1. (B) Genomic location of cDNA clones. Restriction sites in parenthesis at the ends of the cDNA clones indicate linker sequences. Restriction endonuclease sites are: B, BamHI; E, EcoRI; H, HindIII; K, KpnI; P, PstI; and S, SphI.

Chart D.

```
P   H    E  K  S  B    H  H E
|   |    |  |  |  |    |  | |          POLY A
..|___|____|__|__|__|____|__|_|

|_____|     2.4 Kb
                  |_____|     4.2 Kb
              |_____|     4.8 Kb
```

Physical map of the genomic areas from which the FCV subgenomic RNAs are derived. The solid lines indicate regions that are present in the subgenomic RNA. The dotted areas of the lines indicate regions in which transcription initiation may originate based on the length of the transcripts and the mapping hybridization data.

We claim:

1. A pure and isolated polypeptide having the amino acid sequence of the Feline Calicivirus precursor capsid protein as follows:

1   MCSTCANVLK  YYDWDPHIKL  VINPNKFLHV
    GFCDNPLMCC  YPELLPEFGT
51  MWDCDQSPLQ  VYLESILGDD  EWSSTHEAID
    PVVPPMHWDE  AGKIFQPHPG
101 VLMHHLICKV  AEGWDPNLPL  FRLEADDGSI
    TTPEQGTMVG  GVIAEPNAQM
151 STAADMATGK  SVDSEWEAFF  SFHTSVNWST
    SETQGKILFK  QSLGPLLNPY
201 LTHLAKLYVA  WSGSVDVRFS  ISGSGVFGGK
    LSAIVVPPGI  DPVQSTSMLQ
251 YPHVLFDARQ  VEPVIFSIPD  LRSTLYHLMS
    DTDTTSLVIM  VYNPLINPYA
301 NDSNSSGCIV  TVETKPGPDF  KFHLLKPPGS
    MLTHGSIPSD  LIPKSSSLWI
351 GNRFWSDITD  FVIRPFVFQA  NRHFDFNQET
    AGWSTPRFRP  ITITISVKES
401 AKLGIGVATD  YIVPGIPDGW  PDTTIPGELV
    PVGDYAITNG  TNNDITTAAQ
451 YDAATEIRNN  TNFRGMYICG  SLQRAWGDKK
    ISNTAFITTG  TVDGAKLIPS
501 NTIDQTKIAV  FQDTHANKHV  QTSDDTLALL
    GYTGIGEEAI  GADRDRVVRI
551 SVLPERGARG  GNHPIFHKNS  IKLGYVIRSI DVFN-
    SQILHT SRQLSLNHYL
601 LSPDSFAVYR  IIDSNGSWFD  IGIDNDGFSF VGVS-
    SIGKLE FPLTASYMGI
651 QLAKIRLASN  IRSVMTKL.

2. A vaccine comprising the polypeptide according to claim 1 and a pharmaceutically acceptable carrier.

3. A method of protecting an animal susceptible to Feline Calicivirus infection from said infection, comprising administering the vaccine of claim 2 to the animal.

4. The method according to claim 3, wherein said animal is a feline.

* * * * *